(12) United States Patent
Zhang et al.

(10) Patent No.: US 10,273,481 B2
(45) Date of Patent: Apr. 30, 2019

(54) SIRNA IN TANDEM EXPRESSION AND USES THEREOF IN TREATING CHRONIC LYMPHOCYTIC LEUKEMIA

(71) Applicant: Jiangsu Micromedmark Biotech Co., LTD., Jiangsu (CN)

(72) Inventors: Chenyu Zhang, Beijing (CN); Ke Zeng, Beijing (CN); Hongwei Gu, Jiangsu Province (CN); Xueliang Wang, Jiangsu (CN)

(73) Assignee: Jiangsu Mircromedmark Biotech Co., LTD., Jiangsu (CN)

( * ) Notice: Subject to any disclaimer, the term of this patent is extended or adjusted under 35 U.S.C. 154(b) by 139 days.

(21) Appl. No.: 15/115,041

(22) PCT Filed: Jan. 29, 2015

(86) PCT No.: PCT/CN2015/071857
§ 371 (c)(1),
(2) Date: Oct. 28, 2016

(87) PCT Pub. No.: WO2015/113511
PCT Pub. Date: Aug. 6, 2015

(65) Prior Publication Data
US 2017/0044549 A1    Feb. 16, 2017

(30) Foreign Application Priority Data
Jan. 29, 2014   (CN) .......................... 2014 1 0043517

(51) Int. Cl.
*C12N 15/113*    (2010.01)
*C12N 15/11*    (2006.01)

(52) U.S. Cl.
CPC ........ *C12N 15/1137* (2013.01); *C12N 15/111* (2013.01); *C12N 2310/14* (2013.01); *C12N 2310/531* (2013.01); *C12N 2330/51* (2013.01)

(58) Field of Classification Search
None
See application file for complete search history.

(56) References Cited

U.S. PATENT DOCUMENTS 9,637,554 B2 *  5/2017  Conklin ................ C07K 16/40
2005/0246794 A1 * 11/2005  Khvorova ............ A61K 31/713
                                                                       800/286

FOREIGN PATENT DOCUMENTS

| CN | 101684478 A | 3/2010 |
| CN | 102154290 A | 8/2011 |
| WO | WO 2004/013310 A2 | 2/2004 |
| WO | WO 2007/121347 A2 | 10/2007 |

OTHER PUBLICATIONS

GenBank Accession No. BP429187 [online]. [retrieved on May 18, 2018]. retrieved from the Internet: <https:www.ncbi.nlm.nih.gov/nucest/BP429187.1?report=genbank>. (Year: 2011).*
PCT/CN2015/071857, May 11, 2015, International Search Report and Written Opinion.
PCT/CN2015/071857, Aug. 11, 2016, International Preliminary Report on Patentability.

* cited by examiner

*Primary Examiner* — Jennifer Pitrak McDonald
(74) *Attorney, Agent, or Firm* — Wolf, Greenfield & Sacks, P.C.

(57) ABSTRACT

Provided is an siRNA in tandem expression and uses thereof in treating chronic lymphocytic leukemia, and particularly, provided are a method of a tandem expression for siRNA of BTK, and an siRNA in tandem expression and uses thereof in treating chronic lymphocytic leukemia.

13 Claims, 4 Drawing Sheets

Specification includes a Sequence Listing.

SIRNA IN TANDEM EXPRESSION AND USES THEREOF IN TREATING CHRONIC LYMPHOCYTIC LEUKEMIA

RELATED APPLICATIONS

This application is a national stage filing under 35 U.S.C. § 371 of international PCT application PCT/CN2015/071857, filed Jan. 29, 2015, which claims priority to Chinese Application No. 201410043517.9, filed Jan. 29, 2014. Each of the prior applications is incorporated by reference in its entirety.

TECHNICAL FIELD

The present invention pertains to the medical field, more particularly, pertains to a method to tandem-express BTK-specific siRNAs, tandem-expressing siRNAs and the use thereof in the treatment of chronic lymphocytic leukemia.

BACKGROUND ART

Chronic lymphocytic leukemia, CLL in short, is a disease of abnormal mature B lymphocyte proliferation with slow progression.

In over a half of CLL cases exist the homozygosity or heterozygosity loss of 13q14, one of the most common chromosome abnormality of CLL, which features the abnormal proliferation and storage of lymphocytes, accompanied by low immune function. CLL is mostly seen with middle-aged or old people, of whom 90% are over 50, and more liable are the males. The onset of CLL is concealed, and the clinical features are various, inert or invasive. The patients can expect a survival time of 1 to over 15 years. And the pathogenesis of CLL is not quite clear yet.

Presently the knowledge on the prognosis of CLL is limited, so that the treatment measures cannot be adopted as that is with acute leukemia, according to the prognosis risk of patients. The expected survival time of patients even with the worst prognosis can be years.

The factors to be considered in treatment include disease progression, clinical symptoms, tumor load, age, complications, adverse prognostic factors and effect of treatment on survival time, and etc. No effective treatment measures against CLL exist but the hemopoietic stem cell transplant. A typical treatment plan of CLL in hospitals mainly adopt chemotherapy, radiotherapy, interferon therapy and marrow transplant, and etc., but no ideal treatment effect can be realized, and the natural process of the disease cannot be altered.

Therefore, it is an urgent need in the field to develop novel methods and drugs for the effective cure of CLL.

CONTENT OF THE INVENTION

The present invention provides a method for the treatment of CLL and the related drugs.

In the first aspect of the present invention, provided is a reconstructed nuclein sequence to inhibit Bruton's agammaglobulinemia tyrosine kinase (BTK), of which the structure is shown as Formula V:

A-(B-L-)p-Z     (Formula V)

In which,

A represents a random sequence of the 5' end (the length thereof is preferably 0-50 bp, more preferably 0-20 bp, and most preferably 0-10 bp);

B represents the same or different siRNA sequences that specifically inhibit BTK, or the precursor RNA sequences that are used to produce the said siRNA sequences;

L represents random interval sequences (the length thereof is preferably 0-50 bp, more preferably 0-20 bp, and most preferably 0-10 bp);

p is a positive integer amongst 1, 2, 3, 4 or 5;

Z represents a random sequence of the 5' end (the length thereof is preferably 0-50 bp, more preferably 0-20 bp, and most preferably 0-10 bp);

In another preferred example, the said nucleotide sequence includes DNA or RNA sequences.

In another preferred example, the said B is a siRNA, of which the sequence is chosen from SEQ ID NO.: 1, 2 or 3, or a precursor RNA that is to produce the said siRNA.

In another preferred example, the said reconstructed nuclein sequence that inhibits BTK is one or several active ingredients selected from the following group:

(a) BTK inhibiting-siRNAs, of which the said siRNA sequences include siRNA sequences as said in SEQ ID NO.: 1-3;

(b) Precursor RNAs, which can be processed in the host into the BTK inhibiting-siRNAs as said in (a);

(c) Polynucleotides, which can be transcribed in the host into the precursor RNAs as said in (b), and then processed into the siRNAs as said in (a);

(d) Expression vectors, which contain the BTK inhibiting-siRNAs as said in (a), or the precursor RNAs as said in (b), or the polynucleotides as said in (c), and in the said Formula V, A and Z are connected, forming a circular shape.

In another preferred example, the said nucleotide sequence is a nucleotide sequence that co-expresses 2 or several types of siRNAs, which are the same or different.

In another preferred example, the said "reconstructed" includes the artificially synthesized.

In another preferred example, the said primer RNA can be processed in the host (for example, mammals, including humans) into the siRNA as said in (a).

In the second aspect of the present invention, provided is a pharmaceutical composition that comprises of a pharmaceutically acceptable carrier and one or several active ingredients with effective dose and selected from the following group:

(a) BTK inhibiting-siRNAs, of which the said siRNA sequences include siRNA sequences as said in SEQ ID NO.: 1-3;

(b) Precursor RNAs, which can be processed in the host into the BTK inhibiting-siRNAs as said in (a);

(c) Polynucleotides, which can be transcribed in the host into the precursor RNAs as said in (b), and then processed into the siRNAs as said in (a);

(d) Expression vectors, which contain the BTK inhibiting-siRNAs as said in (a), or the precursor RNAs as said in (b), or the polynucleotides as said in (c); and (e) Agonists of the siRNAs as said in (a).

In another preferred example, the polynucleotides said in (c) co-express the said siRNAs that are the same or different.

In another preferred example, the said siRNAs in (a) include forms with or without modification.

In another preferred example, the said forms with modification include one or several forms selected from the following group: glycosylation modification of nucleotides, modification on the connection amongst nucleotides, cholesterol modification, locked nucleotide modification, peptide modification, lipid modification, halogen modification, alkyl modification and nuclein modification.

In another preferred example, the said glycosylation modification of nucleotides includes glycosylation modification of 2-O-methyl, 2-O-methylethyl, 2-O-alkyl, 2-fluoro, and glycoconjugate modification, locked nucleotide modification; and/or the said modification on the connection amongst nucleotides includes thiophosphoric acid modification and phosphoric acid alkylation modification.

In another preferred example, the said modification form contains the monomer or the polymer of the compound with the structure as shown in Formula I:

(X)n-(Y)m                                      Formula I

In Formula I:

Every X represents the said siRNA in (a);

Every Y represents respectively modifications that promote the administration stability of siRNAs;

Y is connected at the left side, right side or middle of X;

n is a positive integer in 1-100 (more preferably 1-20) (more preferably n is 1, 2, 3, 4 or 5);

m is a positive integer in 1-1000 (more preferably 1-200);

Every "-" represents a connector, chemical bond, or covalent bond.

In another preferred example, the said connector is a nucleotide sequence with a length of 1-10 bases.

In another preferred example, the said Y includes (but is not limited to) cholesterol, steroid, sterol, alcohol, organic acid, aliphatic acid, ester, monosaccharide, polysaccharide, amino acid, polypeptide, mononucleotide, polynucleotide.

In another preferred example, the sequence of the said polynucleotide in (c) is as shown in SEQ ID NO.: 7.

```
                                              (SEQ ID NO.: 7)
TTCACTGGACTCTTCACCTCTGTTTTGGCCACTGACTGACAGAGGTG

AAGTCCAGTGAACAGGACACAAGGCCTGTTACTAGCACTCACATGGAAC

AAATGGCCCAGATCCTGGAGGCTTGCTGAAGGCTGTATGCTGTTAGCAGT

TGCTCAGCCTGACGTTTTGGCCACTGACTGACGTCAGGCTGCAACTGCTA

ACAGGACACAAGGCCTGTTACTAGCACTCACATGGAACAAATGGCCCAG

ATCCTGGAGGCTTGCTGAAGGCTGTATGCTGAACAGTTTCGAGCTGCCAG

GTGTTTTGGCCACTGACTGACACCTGGCATCGAAACTGTT
```

In which, the sequence of SEQ ID NO.: 7 is a polynucleotide sequence with tandem-connected BTK-1-2-3, in which:

The sequence of the polynucleotide relating to BTK-1 (i.e., DNA sequence that encodes the precursor RNA) is:

```
                                              (SEQ ID NO.: 4)
TTCACTGGACTCTTCACCTCTGTTTTGGCCACTGACTGACAGAGGTG

AAGTCCAGTGAA;
```

The sequence of the polynucleotide relating to BTK-2 (i.e., DNA sequence that encodes the precursor RNA) is:

```
                                              (SEQ ID NO.: 5)
TTAGCAGTTGCTCAGCCTGACGTTTTGGCCACTGACTGACGTCAGGC

TGCAACTGCTAA;
```

The sequence of the polynucleotide relating to BTK-3 (i.e., DNA sequence that encodes the precursor RNA) is:

```
                                              (SEQ ID NO.: 6)
AACAGTTTCGAGCTGCCAGGTGTTTTGGCCACTGACTGACACCTGGCATC

GAAACTGTT.
```

And the siRNA sequences of the 3 BTKs are as follows:

```
                                              (SEQ ID NO.: 1)
BTK-1: UUCACUGGACUCUUCACCUCU;

(SEQ ID NO.: 2)
BTK-2: UUAGCAGUUGCUCAGCCUGAC;

(SEQ ID NO.: 3)
BTK-3: AACAGUUUCGAGCUGCCAGGU.
```

In another preferred example, the polynucleotide said in (c) comprises one or several structure units as shown in Formula II:

$Seq_{forward}$-X-$Seq_{backward}$                 Formula II

In Formula II, $Seq_{forward}$ is a nucleotide sequence that can be processed in the host into the said microRNA;

$Seq_{backward}$ is a nucleotide sequence that is substantially or completely complementary with the $Seq_{forward}$;

X is an interval sequence between the $Seq_{forward}$ and $Seq_{backward}$, and is not complementary therewith;

Being transferred into the host cell, the structure shown in Formula II will form a secondary structure as shown in Formula III:

Formula III

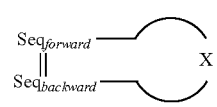

In Formula III, the $Seq_{forward}$ and $Seq_{backward}$ and X are defined as above;

|| represents the base complementary relationship between the $Seq_{forward}$ and $Seq_{backward}$;

And the $Seq_{forward}$s in each construct unit can be the same or different.

In another preferred example, the expression vector said in (d) includes: viral vector or non-viral vector.

In another preferred example, the agonist of BTK-inhibiting siRNAs is selected from the following group: substance that promotes the expression of BTK-inhibiting siRNAs, substance that promotes the activity of BTK-inhibiting siRNA.

In the third aspect of the present invention, provided is the use of an active ingredient, which is selected from the following group:

(a) BTK inhibiting-siRNAs, of which the said siRNA sequences include siRNA sequences as said in SEQ ID NO.: 1-3;

(b) Precursor RNAs, which can be processed in the host into the BTK inhibiting-siRNAs as said in (a);

(c) Polynucleotides, which can be transcribed in the host into the precursor RNAs as said in (b), and then processed into the siRNAs as said in (a);

(d) Expression vectors, which contain the BTK inhibiting-siRNAs as said in (a), or the precursor RNAs as said in (b), or the polynucleotides as said in (c); and (e) Agonists of the siRNAs as said in (a).

The said active ingredient is used to prepare drugs for the inhibition of BTKs, or the prevention or treatment of CLL.

In another preferred example, the said active ingredient is the polynucleotide as said in (c), and the said polynucleotides co-express the said siRNAs that are the same or different.

In another preferred example, the said polynucleotides co-express the siRNAs shown by SEQ ID NO.: 1, 2 and 3.

In the fourth aspect of the present invention, provided is a method for the prevention or treatment of CLL, administering the subject in need with safe and effective dose the medical composition as said in the second aspect, and the re-constructed, BTK-inhibiting nucleotide sequence as said in the first aspect of the present invention.

It shall be understood that, within the scope of the present invention, the aforesaid technical features and the technical features as specified in the following content (e.g., in the examples) can be combined with each other, so as to form new or more preferable technical strategy. For the economy of words, the combinations will not be listed herein one by one.

Figure 1:
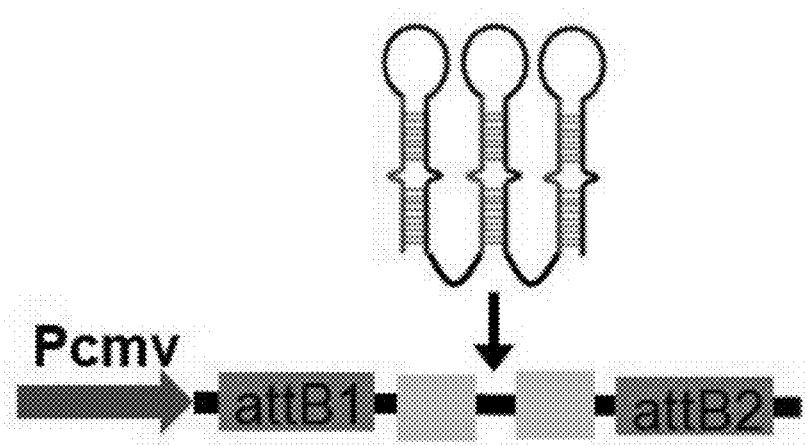
FIG. 1 shows the construct of the co-expressing siRNA in one example of the present invention.

In each figure, "control" represents the control, "mock" represents the blank control; "nc" represents being transfected with blank expression vectors (the negative control); "plasmid-1" represents that the transfected P1 plasmid can express BTK-1, "plasmid-2" represents that the transfected P2 plasmid can express BTK-2, "plasmid-3" represents that the transfected P3 plasmid can express BTK-3, and "plasmid-1-2-3" represents that the transfected P1-2-3 plasmid can express BTK1-2-3.

Particular Embodiments

The inventors discover through wide and in-depth researches and massive screening of nucleotide sequences that certain siRNAs possess rather strong BTK inhibition ability, and when they are tandem-expressed, the inhibition effect is even stronger. Therefore, the expression and activity of BTK can be effectively inhibited through importing the siRNAs that specifically inhibit BTK; thereby CLL can be prevented and treated. The present invention is completed on this basis.

Active Ingredients of the Present Invention

As used herein, the "active ingredients of the present invention" refer to one or more kinds of active ingredients selected from the following group (including the combination thereof):

(a) BTK-inhibiting siRNAs, the sequence of which comprises any of the siRNA sequences as said in SEQ ID NO.: 1-3 (including the combination thereof);

(b) Precursor RNAs, which can be processed in the host into the BTK inhibiting-siRNAs as said in (a);

(c) Polynucleotides, which can be transcribed in the host into the precursor RNAs as said in (b), and then processed into the siRNAs as said in (a);

(d) Expression vectors, which contain the BTK inhibiting-siRNAs as said in (a), or the precursor RNAs as said in (b), or the polynucleotides as said in (c); and (e) Agonists of the siRNAs as said in (a).

SiRNAs and Precursors Thereof

The present invention provides a type of siRNA for the treatment of CLL. As used herein, the said "siRNA" refers to a type of RNA molecules, which can be processed with the transcription product that can form the siRNA precursors. Mature siRNAs usually comprise 18-26 nucleotides (nt) (more particularly, 19-22 nt), not excluding other numbers of nucleotides. The siRNAs can usually be detected with Northern blotting.

As used herein, "isolated" refers to that a substance is isolated from its original environment (if the substance is a natural substance, its original environment is the natural environment). For example, the polynucleotides and polypeptides in a living cell are not isolated and purified in the natural state, but the same polynucleotides and polypeptides are isolated and purified when they are isolated from the other substances co-existing in the natural state.

It shall be notified that siRNAs are usually produced through simulating the production mechanism of miRNAs. The siRNAs can be processed from precursor RNAs (pre-RNAs). The said pre-RNAs can fold into a stable stem-loop (hairpin) structure, of which the length is usually within 50-100 bp. The two sides of the stem part of the said stem-loop structure comprise two sequences that are substantially complementary. The said pre-RNA can be natural occurring or artificially synthesized.

The pre-RNA can be cut to generate siRNA. And said siRNA may be substantially complementary to at least a portion of the sequence of the mRNA encoding the gene. As used herein, "substantially complementary" means that the nucleotide sequence is sufficiently complementary and can act upon each other in a predictable manner, e.g., forming a secondary structure (such as a stem-loop structure). Generally, at least 70% of nucleotides in two "substantially complementary" nucleotide sequences are complementary; preferably, at least 80% of nucleotides are complementary;

more preferably, at least 90% of nucleotides are complementary; and further preferably, at least 95% of nucleotides are complementary, e.g., 98%, 99% or 100%. Generally, there are at most 40 non-matched nucleotides between two sufficiently complementary molecules; preferably, there are at most 30 non-matched nucleotides; more preferably, there are at most 20 non-matched nucleotides; and further preferably, there are at most 10 non-matched nucleotides, e.g., there are 1, 2, 3, 4, 5 or 8 non-matched nucleotides.

As used herein, "stem-loop" structure is also named "hairpin" structure, referring to a type of nucleotide molecule that can form a secondary structure with a double-strand area (stem). The said double-strand area is formed by two parts of the nucleotide molecule (locating at the same molecule), and the said two parts are located respectively at two sides of the double-strand area; at least one "loop" structure is also included, which comprises non-complementary nucleotide molecules, i.e., the single-strand area. Even when the two parts of the nucleotide molecule is not completely complementary; the double-strand part thereof can keep the double-strand state. For example, insertion, absence, replacement in a small area can cause non-complement or formation of stem-loop structure or other kinds of secondary structures. However, the two areas can still complement with each other and react in a predictable manner, forming the double-strand area of the stem-loop structure. The stem-loop structure is commonly known by the skilled person in the art. Usually when being given a nucleic acid with nucleotide sequence of the first structure, a skilled person in the art can determine whether the nucleic acid can form the stem-loop structure.

The siRNAs said in the present invention refer to: micro RNAs of the BTK-inhibiting family, which include BTK-inhibiting siRNAs or modified BTK-inhibiting siRNA derivatives.

In one preferred example of the present invention, the nucleotide sequence of the BTK-inhibiting siRNAs is shown as SEQ ID NO.: 1, 2 and 3. Most preferably is SEQ ID NO.: 3.

The present invention also includes siRNA variants and derivatives. Meanwhile, siRNA derivatives in the broader sense can also include siRNA variants. The ordinary skilled person in the art can modify the BTK-inhibiting siRNAs using conventional methods, including (but not being limited to): methylation modification, alkyl modification, glycosylation modification (such as 2-methoxy-glycosyl modification, alkyl-glycosyl modification, glycoconjugate modification and etc.), nucleination modification, peptide modification, lipid modification, nuclein modification (such as "TT" modification).

Polynucleotide Construct

Basing on the siRNA sequence provided in the present invention, polynucleotide constructs can be designed, which can be processed into siRNAs that, being imported, can affect the expression of related mRNAs. Therefore, the present invention provides a type of isolated polynucleotide (construct), which can be transcribed in the human cell into precursor RNAs that can be cut in the human cell and expressed as the said siRNAs.

As one preferable embodiment of the present invention, the said polynucleotide construct comprises one or more structure units as shown in Formula II:

$$Seq_{forward}\text{-}X\text{-}Seq_{backward} \qquad \text{Formula II}$$

In Formula II, $Seq_{forward}$ is a nucleotide sequence that can be expressed in cells into the said BTK-inhibiting siRNA, $Seq_{backward}$ is a nucleotide sequence that is substantially complementary with $Seq_{forward}$; or, $Seq_{backward}$ is the nucleotide sequence that can be expressed in cells into the said BTK-inhibiting siRNA, $Seq_{forward}$ is the nucleotide sequence that is substantially complementary with $Seq_{backward}$; X is a spacer sequence between $Seq_{forward}$ and $Seq_{backward}$. The said spacer sequence is complementary to neither $Seq_{forward}$ nor $Seq_{backward}$.

In which, each structure unit can express the same or different siRNAs;

Being transferred into cells, the structure shown in Formula I will form a secondary structure as shown in Formula III:

Formula III

In Formula III, the $Seq_{forward}$ and $Seq_{backward}$ and X are defined as above;

|| represents the base complementary relationship between the $Seq_{forward}$ and $Seq_{backward}$;

The said polynucleotide construct is usually placed in an expression vector. Therefore, the present invention also includes an expression vector that contains the said siRNA or the said polynucleotide construct. The said expression vector usually comprises of a promoter, origin of replication and/or marker genes, and etc. Methods commonly known by the skilled persons in the art can be used to construct the expression vector needed in the present invention. These methods include DNA in vitro reconstruct, DNA synthesis and DNA in vivo reconstruct techniques, and etc. The said expression vector comprises preferably of one or several marker genes, such as resistance against kalamycin, gentamycin, hygromycin, ampicillin, so as to enable the selection of phenotypic characteristics of transformed host cells.

Bruton's Agammaglobulinemia Tyrosine Kinase (Btk)

Bruton's agammaglobulinemia tyrosine kinase, Btk, is a member of the non-receptor tyrosine family. It comprises of 5 domains: the Pleckstr inhomology domaIn (PH domain), Tec homology domain (TH domain), Src homology3 domain (SH3 domain), Src homology2 domain (SH2 domain) and Tyrosine kinase domain (catalytic domain).

Tyrosine kinases can be classified according to their location in cells two kinds, receptor tyrosine kinases and non-receptor tyrosine kinases. The receptor tyrosine kinases locate on the cell membrane, being the receptor and enzyme at the same time. The non-receptor tyrosine kinases locate in the cytoplasma or nucleus. They are divided according to their homology into 11 families including Tec, AB1 and Ack, and etc. Btk belongs to the Tec family of non-receptor tyrosine kinases. The domains can identify and combine with various signal molecules, providing structural foundation for the participation of Btk in multiple signal pathways.

The protein encoded by Btk is a cytoplasmic protein, so that the Btk protein is expressed by, except for T lymphocytes and phlogocytes from the development end of B lymphocytes, all other myeloid cells, including B lymphocytes, basophile granulocytes and monocytes, and etc., and is stably expressed during the whole development process of B lymphocytes. The survival and migration of malignant tumor cells mainly depends on the antigen receptor signal of B lymphocytes. In the signal pathway, Btk is an essential signal.

The amino acid and nucleotide sequence of human Btk is registered in Genbank under the number of NM_000061.

Pharmaceutical Compositions

The present invention provides a pharmaceutical composition that comprises of a pharmaceutically acceptable carrier and one or several active ingredients of the present invention with effective dose.

In another preferred example, the said modified siRNA derivative contains the monomer or the polymer of the compound with structure as shown in Formula I:

(X)n-(Y)m             Formula I

In Formula I, each X is a siRNA said in (a); each Y is an independent modifier promoting the administration stability of small RNAs; n is a positive integer in 1-100 (preferably 1-20), (n is preferably 1, 2, 3, 4 or 5); m is a positive integer in 1-1000 (preferably 1-200); each "-" represents a connector, chemical bond or covalent bond; in another preferred example, the said connector is a nucleotide sequence with a length of 1-10 bases. The said Y includes (but is not limited to) cholesterol, steroid, sterol, alcohol, organic acid, aliphatic acid, ester, monosaccharide, polysaccharide, amino acid, polypeptide, mononucleotide, polynucleotide.

In another preferred example of the present invention, the polynucleotide said in (c) comprises one or several structure units as shown in Formula II:

Seq$_{forward}$-X-Seq$_{backward}$             Formula II

In Formula II, Seq$_{forward}$ is a nucleotide sequence that can be expressed in cells into the said BTK-inhibiting siRNA, Seq$_{backward}$ is a nucleotide sequence that is substantially complementary with Seq$_{forward}$; or, Seq$_{backward}$ is the nucleotide sequence that can be expressed in cells into the said BTK-inhibiting siRNA, Seq$_{forward}$ is the nucleotide sequence that is substantially complementary with Seq$_{backward}$; X is a spacer sequence between Seq$_{forward}$ and Seq$_{backward}$. The said spacer sequence is complementary to neither Seq$_{forward}$ nor Seq$_{backward}$. And being transferred into the host cell, the structure shown in Formula II can transform into a secondary structure as shown in Formula III:

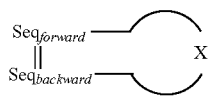

Formula III

In Formula III, Seq$_{forward}$, Seq$_{backward}$ and X are defined as said above, ∥ represents the base complementary relationship between the Seq$_{forward}$ and Seq$_{backward}$;

In another preferred example of the present invention, the corresponding DNA sequence of encoding primer RNA is shown as SEQ ID NO. 7 and 4-6:

```
                                            (SEQ ID NO.: 7)
TTCACTGGACTCTTCACCTCTGTTTTGGCCACTGACTGACAGAGGTG

AAGTCCAGTGAACAGGACACAAGGCCTGTTACTAGCACTCACATGGAAC

AAATGGCCCAGATCCTGGAGGCTTGCTGAAGGCTGTATGCTGTTAGCAGT

TGCTCAGCCTGACGTTTTGGCCACTGACTGACGTCAGGCTGCAACTGCTA

ACAGGACACAAGGCCTGTTACTAGCACTCACATGGAACAAATGGCCCAG

ATCCTGGAGGCTTGCTGAAGGCTGTATGCTGAACAGTTTCGAGCTGCCAG

GTGTTTTGGCCACTGACTGACACCTGGCATCGAAACTGTT
```

In which, the sequence of SEQ ID NO.: 7 is a polynucleotide sequence with tandem-connected BTK-1-2-3, in which:

The sequence of the polynucleotide relating to BTK-1 (i.e., DNA sequence that encodes the precursor RNA) is:

```
                                            (SEQ ID NO.: 4)
TTCACTGGACTCTTCACCTCTGTTTTGGCCACTGACTGACAGAGGTGA

AGTCCAGTGAA;
```

The sequence of the polynucleotide relating to BTK-2 (i.e., DNA sequence that encodes the precursor RNA) is:

```
                                            (SEQ ID NO.: 5)
TTAGCAGTTGCTCAGCCTGACGTTTTGGCCACTGACTGACGTCAGGCT

GCAACTGCTAA;
```

The sequence of the polynucleotide relating to BTK-3 (i.e., DNA sequence that encodes the precursor RNA) is:

```
                                            (SEQ ID NO.: 6)
AACAGTTTCGAGCTGCCAGGTGTTTTGGCCACTGACTGACACCTGGCAT

CGAAACTGTT.
```

As used herein, the term "effective amount" or "effective dose" refers to the amount, with which a composition can take effect on and be accepted by humans and/or animals.

As used herein, "pharmaceutically acceptable" ingredient refers to an ingredient that is applicable on humans and/or mammals without excessive adverse side effects (such as toxicity, stimulation and allergic reaction), i.e., ingredient with sensible benefit/risk ratio. The term "pharmaceutically acceptable carrier" refers to the carrier for the effect ingredient, including all sorts of excipients and diluents.

The pharmaceutical composition of the present invention comprises the active ingredient of the present invention of the safe effect amount and a pharmaceutically acceptable carrier. The carriers include (but are not limited to): saline water, buffer, glucose, water, glycerol, ethanol, and a combination thereof. Generally, a pharmaceutical preparation shall match with the form of administration, and the dosage form of the pharmaceutical composition of the present invention can be injection, oral preparation (tablet, capsule, or oral liquid), transdermal agent, or sustained release agent. For example, preparation is performed with a conventional method using physiological saline or an aqueous solution containing glucose and other adjuvants. Said pharmaceutical composition is preferably produced under sterile conditions.

The effective amount of the active ingredient of the present invention may vary depending on the mode of administration and the severity of the disease to be treated. A person skilled in the art could determine the selection of the preferred effective amount depending on various factors (e.g., by clinical trials). Said factors include, but are not limited to, the pharmacokinetic parameters of said active ingredient, e.g., bioavailability, metabolism, half-life, etc.; and the severity of the patient's disease to be treated, the patient's weight, the patient's immune state, the administration route, etc. Generally, when the active ingredient of the present invention is administered at a dose of about 0.00001-50 mg/kg body weight (preferably 0.0001-10 mg/kg body weight) per day, satisfactory results can be achieved. For example, due to the urgent requirements of the treatment status, several separate doses can be administered on one day, or the dosage can be proportionally reduced.

In the present invention, the said pharmaceutically acceptable carriers include but are not limited to: water, saline solution, liposomes, lipids, proteins, protein-antibody complex, peptides, cellulose, nanogel, or the combination thereof. The choice of carriers should match the mode of administration, which is well known to an ordinary person skilled in the art.

The said active ingredient is used to prepare pharmaceutical compositions for the inhibition of BTKs, or the prevention or treatment of CLL.

Prevention or Treatment Method

The present invention provides a method to prevent or treat CLL.

In one preferred example, the said method includes administrating to subjects in need the pharmaceutical composition of the present invention with safe and effective dose; or administrating the active ingredient of the present invention with safe and effective dose.

The main advantages of the present invention include:
1) Validates an essential type of siRNA sequences specific to BTK;
2) tandem-expresses BTK-specific siRNAs;
3) Provides a method to treat CLL targeting BTK, while validates that BTK-siRNA can be expressed in the cell using the generation mechanism of miRNAs.

The present invention is further illustrated in connection with particular embodiments as follows. It should be understood that these embodiments are merely illustrative of the invention and are not intended to limit the scope of the present invention. In the case of specific conditions for the experimental method being not specified in the following examples, generally conventional conditions are followed, such as the conditions described in Sambrook et al., *Molecular Cloning: A Laboratory Manual* (New York: Cold Spring Harbour Laboratory Press, 1989), or the conditions recommended by the manufacturer are followed. All percentages and portions are of weight unless otherwise indicated.

EXAMPLE 1

Tandem-expression of BTK-specific siRNAs
1. Experiment method
1.1 Construction of interference plasmid In this example, 3 siRNAs are designed targeting the BTK gene, i.e., BTK-1, BTK-2 and BTK-3, of which the sequences are:

```
                                        (SEQ ID NO.: 1)
BTK-1: UUCACUGGACUCUUCACCUCU;

(SEQ ID NO.: 2)
BTK-2: UUAGCAGUUGCUCAGCCUGAC;

(SEQ ID NO.: 3)
BTK-3: AACAGUUUCGAGCUGCCAGGU.
```

The expression precursors of the above-said 3 siRNAs are capsuled in the miRNA expression vector, so as to express the siRNAs in the form of miRNAs, constructing plasmids: P1, P2 and P3 respectively.

Meanwhile, 3 BTK siRNAs are tandem-expressed (comprising of 3 hairpin structures), so as to avoid adverse situations such as accidental off-target effect, constructing tandem-plasmid P1-2-3.

In which, the structure of polynucleotide sequence to express BTK-1, BTK-2, BTK-3 is shown as FIG. 1, and the said sequence is shown as the following:

```
                                        (SEQ ID NO.: 7)
TTCACTGGACTCTTCACCTCTGTTTTGGCCACTGACTGACAGAGGTG

AAGTCCAGTGAACAGGACACAAGGCCTGTTACTAGCACTCACATGGAAC

AAATGGCCCAGATCCTGGAGGCTTGCTGAAGGCTGTATGCTGTTAGCAGT

TGCTCAGCCTGACGTTTTGGCCACTGACTGACGTCAGGCTGCAACTGCTA

ACAGGACACAAGGCCTGTTACTAGCACTCACATGGAACAAATGGCCCAG

ATCCTGGAGGCTTGCTGAAGGCTGTATGCTGAACAGTTTCGAGCTGCCAG

GTGTTTTGGCCACTGACTGACACCTGGCATCGAAACTGTT
```

In which,
The sequence of the polynucleotide relating to BTK-1 is:

```
                                        (SEQ ID NO.: 4)
TTCACTGGACTCTTCACCTCTGTTTTGGCCACTGACTGACAGAGGTG

AAGTCCAGTGAA;
```

The sequence of the polynucleotide relating to BTK-2 is:

```
                                        (SEQ ID NO.: 5)
TTAGCAGTTGCTCAGCCTGACGTTTTGGCCACTGACTGACGTCAGGC

TGCAACTGCTAA;
```

The sequence of the polynucleotide relating to BTK-3 is:

```
                                        (SEQ ID NO.: 6)
AACAGTTTCGAGCTGCCAGGTGTTTTGGCCACTGACTGACACCTGGC

ATCGAAACTGTT.
```

1.2 Cells

Peripheral blood of CLL patients and normal persons is extracted under sterile conditions and then given with anti-coagulants. Lymphocytes in the peripheral blood are isolated with lymphocyte separation solution on a super clean bench and then rinsed twice with PBS so as to leave the lymphocyte separation solution completely. The remaining red blood cells are lysated with red blood cell lysis buffer. The lymphocytes are finally re-suspended with RPMI-1640+ 15% FBS. Detecting with a flow cytometry determines that B lymphocytes take more than 95% of all. The cells from CLL patients are cultured at 37° C. 5% $CO_2$ for future use.

1.3 Transfection

Cells are processed 1 hour before transfection with exsuction and centrifugation, so as to remove the serum. After re-suspension with serum-free RPMI-1640, the cells are placed on a 12-hole plate and transfected with lipofection 2000 following the methods recommended by the instruction. After 48 h of transfection, the cells are collected.

1.4 Extraction of RNA and Synthesis of cDNA

Total RNA of cells is extracted with TRIzol reagent with the standard method, and then reverse-transcribed into cDNA using oligo dT primer and AMV transcriptase, and β-actin as internal reference.

1.5 Quantitative PCR Detection

Quantitative PCR detection is performed with the primer of BTK and β-actin respectively.

BTK-P1: 5'-GAAGGAGGTTTCATTGTCA-3' (SEQ ID NO.: 8)

BTK-P2: 5'-TAATACTGGCTCTGAGGTGT-3' (SEQ ID NO.: 9)

Annealing temperature: 53° C.

ACT-P1: 5'-CTCCATCCTGGCCTCGCTGT-3' (SEQ ID NO.: 10)

ACT-P1: 5'-GCTGTCACCTTCACCGTTCC-3' (SEQ ID NO.: 11)

Annealing temperature: 52° C., product=268 bp.

1.6 Western Blotting

Centrifugation at 1000 rpm is performed for 5 min, and then the cells are collected and lysated with cell lysis solution, followed by ice bath for 30 min. Then cell debris is removed by centrifugation at 10000 rpm for 10 min. The extract total protein is then quantified, processed with 10% SDS-PAGE and then transferred on PVDV film, so as to be incubated with anti-BTK-specific antibodies. Enzyme-labeled rabbit anti-mouse second antibodies are added, and the protein is detected with the chemiluminescence method.

2. Results 2.1 DETECtion of BTK mRNA expression change with QRT-PCR

TABLE 1

| Control | 1.0000 |
|---------|--------|
| P1      | 0.7899 |
| P2      | 0.7072 |
| P3      | 0.5743 |
| P1-2-3  | 0.4064 |

Figure 2:
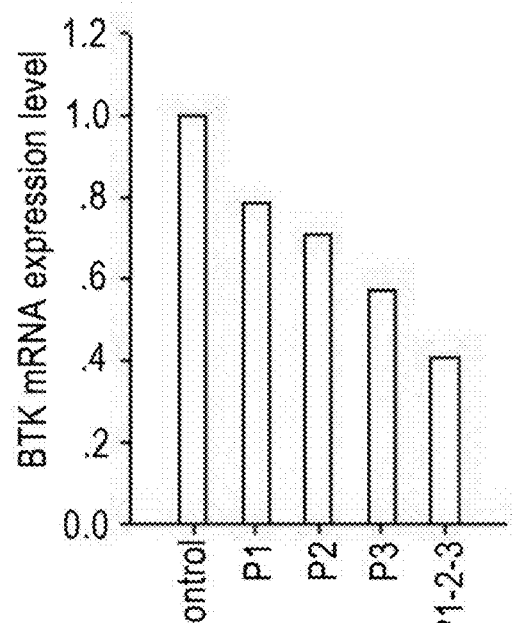
FIG. 2 shows the effect of the siRNA on the expression of BTK mRNA in one example of the present invention.

According to the results of QRT-PCR detection for BTK mRNA expression (as shown in Table 1 and FIG. 2), it can be told that plasmid P1, P2, P3 and P1-2-3 are all effective, while P1-2-3 is the most effective.

It is proved that single siRNA or multiple siRNAs can inhibit the expression of BTK, in which these in the form of tandem-expression functions at the best, followed by BTK-3.

2.2 Detection of BTK protein expression change with western blotting

Figure 3:
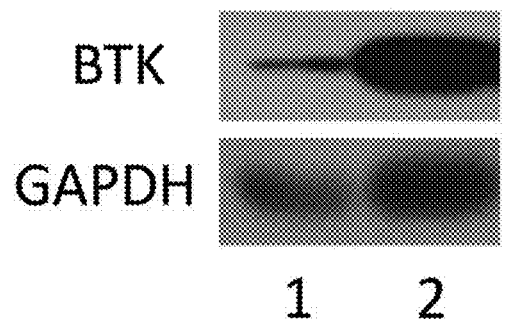
FIG. 3 shows that the BTK expression in the CLL patients is significantly higher than that of the normal persons, in which "1" represents the normal persons, and "2" represents the CLL patients.

As shown in FIG. 3, BTK expression in the CLL patients is significantly higher than that of the normal persons, 2.3 Western blotting validates that a single siRNA or multiple siRNAs can inhibit the expression of BTK.

Figure 4:
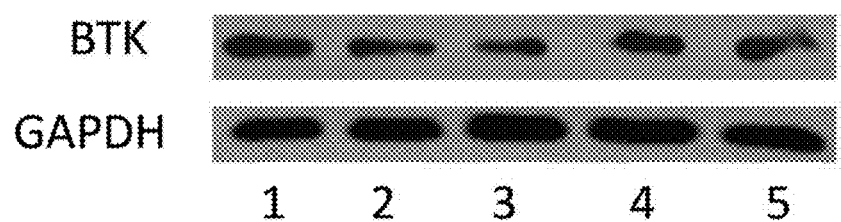
FIG. 4 shows that, being proved with the Western blotting method, the siRNA of the present invention can inhibit the expression of BTK, in which "1" represents the control, "2" represents P1, "3" represents P2, "4" represents P3, and "5" represents P1-2-3.

The detection result of BTK protein expression with Western blotting is as shown in FIG. 4. The results also indicate that plasmids P1, P2, P3 and P1-2-3 (tandem-expression of the three) are all effective in BTK inhibition.

EXAMPLE 2

Effect of BTK siRNA on B Lymphocytes 1.1 Preparation of B lymphocytes

In this example, normal Daudi cells (lymphocytes) are resuscitated, cultured with RPMI-1640+10% FBS, at 37° C. 5% $CO_2$ for future use.

1.2 Transfection

The method is as said in part 1.3 of Example 1.

1.3 Extraction of RNA and synthesis of cDNA

The method is as said in part 1.4 of Example 1.

Figure 1.4 Analysis with the Western Blotting Method on the Effect of BTK siRNA on BTK Protein.

The method is as said in part 1.6 of Example 1.

Figure 5:
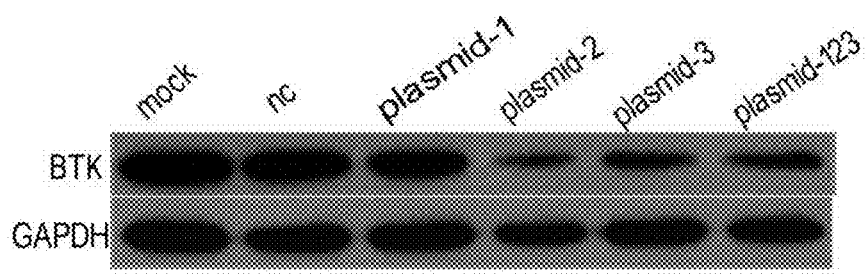
FIG. 5 shows with the Western blotting method the effect of BTK siRNA on BTK protein.
Figure 6:
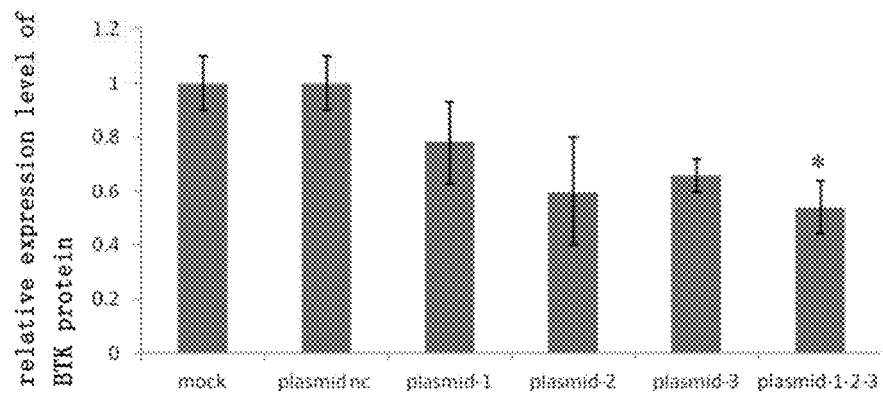
FIG. 6 shows the quantitative analysis results of BTK siRNA on BTK protein.

The detailed results are shown in FIGS. 5 and 6. After the transfection of plasmid-1, plasmid-2, plasmid-3 and plasmid-1-2-3 (tandem of 3 plasmids), the expression of BTK protein reduces, indicating that all of plasmid-1, plasmid-2, plasmid-3 and plasmid-1-2-3 can effectively inhibit BTK, in which the plasmid-1-2-3 in the form of tandem expression is significantly more effective, down-regulating the expression of BTK protein at around 50%, followed by plasmid-2.

1.5 Detection for the effect of BTK siRNA on BTK mRNA with QRT-PCR

Quantitative PCR detection is performed with the primer of BTK and β-actin respectively. The method is as said in part 1.5 of Example 1, but with different primers shown as follows:

BTK primer F15: 5'-TGCTCCCACTCAATACAAA-3' (SEQ ID NO.: 12)

BTK primer R15'-GCTCTACCAAATGCCTACTC-3' (SEQ ID NO.: 13)

Annealing temperature: 53° C.

ACT-P1: 5'-CTCCATCCTGGCCTCGCTGT-3' (SEQ ID NO.: 10)

ACT-P1: 5'-GCTGTCACCTTCACCGTTCC-3' (SEQ ID NO.: 11)

Annealing temperature: 52° C., product=268 bp.

Figure 7:
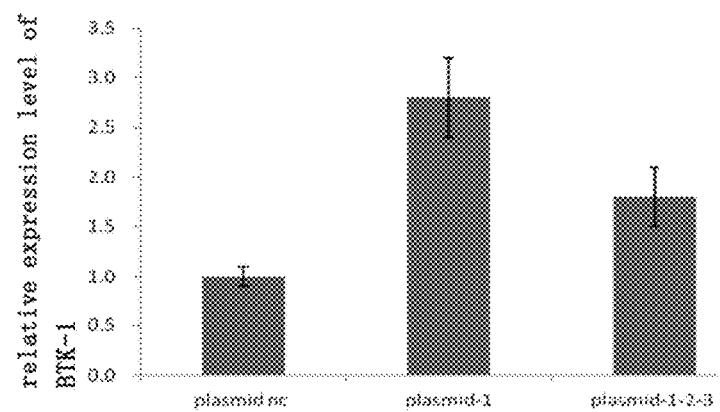
FIG. 7 shows the content of BTK-1 after the transfection of P1 plasmid, in which "plasmid nc" represents being transfected with blank expression vector as the negative control; "plasmid-1" represents that the transfected P1 plasmid can express BTK-1, "plasmid-1-2-3" represents that the transfected P1-2-3 plasmid can express BTK 1-2-3.

The detailed results are shown in FIG. 7, 8, 9, 10.

It can be seen in FIG. 7 that, being compared with transfection of blank plasmid (plasmid nc), the expression of BTK-1 in B lymphocytes is significantly increased with transfection of P1, P1-2-3.

Figure 8:
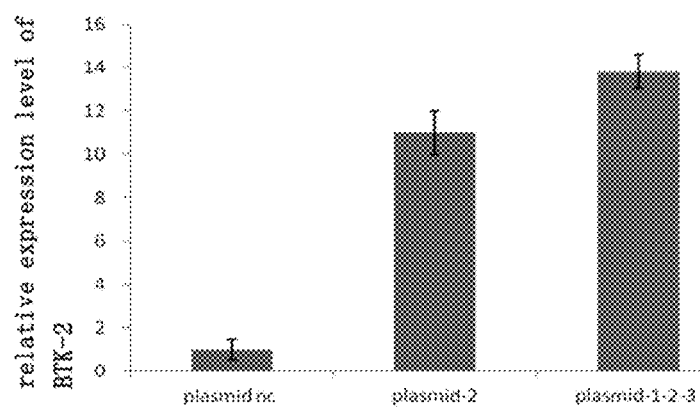
FIG. 8 shows the content of BTK-2 after the transfection of P2 plasmid, in which "plasmid nc" represents being transfected with blank expression vector as the negative control; "plasmid-2" represents that the transfected P2 plasmid can express BTK-2, "plasmid-1-2-3" represents that the transfected P1-2-3 plasmid can express BTK 1-2-3.

It can be seen in FIG. 8 that, being compared with transfection of blank plasmid (plasmid nc), the expression of BTK-2 in B lymphocytes is significantly increased with transfection of P2, P1-2-3.

Figure 9:
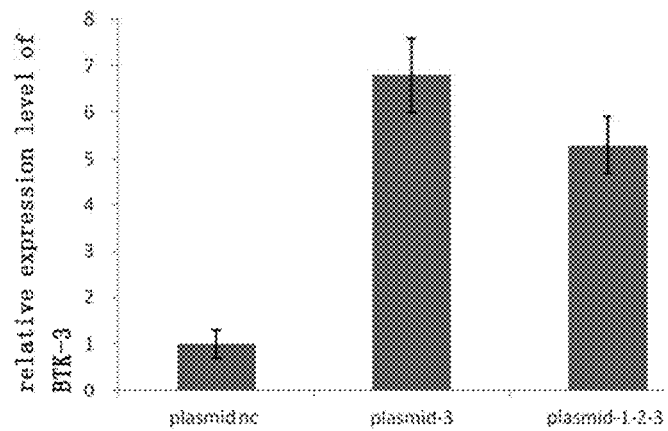
FIG. 9 shows the content of BTK-3 after the transfection of P3 plasmid, in which "plasmid nc" represents being transfected with blank expression vector as the negative control; "plasmid-3" represents that the transfected P3 plasmid can express BTK-3, "plasmid-1-2-3" represents that the transfected P1-2-3 plasmid can express BTK 1-2-3.

It can be seen in FIG. 9 that, being compared with transfection of blank plasmid (plasmid nc), the expression of BTK-3 in B lymphocytes is significantly increased with transfection of P3, P1-2-3.

Figure 10:
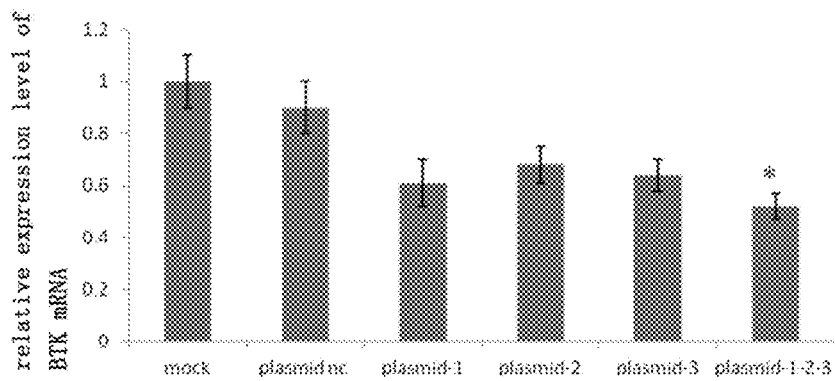
FIG. 10 shows the content of BTK mRNA in the B lymphocytes after the transfection of P1, P2, P3, P1-2-3 plasmids.

It can be seen in FIG. 10 that, with transfection of P1, P2, P3 and P1-2-3 (tandem of 3 plasmids), the expression of BTK mRNA is reduced, indicating that all of P1, P2, P3 and P1-2-3 can effectively inhibit BTK mRNA. Being compared with the control group, the tandem-expression of P1-2-3 is more effective, with the BTK mRNA reduced at around 50%.

In summary, being transfected with BTK siRNA plasmids P1, P2, P3 and P1-2-3, the expression of BTK-1, BTK-2 and BTK-3 siRNA is all increased; the expression of BTK mRNA and BTK protein is decreased. All of BTK-1, BTK-2, BTK-3 and tandem-expressed P1-2-3 can inhibit the BTK gene and protein in B lymphocytes. And the inhibition on the BTK gene and protein in B lymphocytes of the tandem-expressed P1-2-3 is stronger and with better effect.

All the documents mentioned in the present invention are incorporately referred to, as well as each alone. In addition, it should be understood that after reading the teachings of the present invention described above, a skilled person in the art can make various changes or modifications of the invention, and these equivalent forms shall also fall into the scope of the present application as defined by the appended claims.

The invention claimed is:

1. A recombinant nucleic acid molecule for inhibiting Bruton's agammaglobulinemia tyrosine kinase (BTK), wherein the recombinant nucleic acid molecule comprises Formula V:

$$A\text{-}(B\text{-}L)p\text{-}Z \qquad (V),$$

wherein

A is an optional sequence of 0-50 nucleotides (nts) at 5' end,

B is either of
   (1) a BTK-targeted siRNA sequence selected from SEQ ID NO: 1, SEQ ID NO:2, and SEQ ID NO:3, or
   (2) a precursor RNA molecule of Formula II $$\text{Seq}_{forward}\text{-X-Seq}_{backward} \qquad (II),$$

wherein
   $\text{Seq}_{forward}$ or $\text{Seq}_{backward}$ comprises SEQ ID NO:1, SEQ ID NO:2, or SEQ ID NO:3,
   $\text{Seq}_{forward}$ and $\text{Seq}_{backward}$ are capable of hybridizing to each other, and
   X is a loop sequence not complementary to $\text{Seq}_{forward}$ or $\text{Seq}_{backward}$;

L is an optional interval sequence of 0-50 nts;

p is a positive integer of 2, 3, 4, or 5;

Z is an optional sequence of 0-50 nts at 3' end.

2. The recombinant nucleic acid of claim 1, wherein each B is a different sequence.

3. A pharmaceutical composition comprising a pharmaceutically acceptable carrier and an effective amount of one or more active agents selected from the group consisting of:
   (a) the recombinant nucleic acid molecule of claim 1,
   (b) a polynucleotide that encodes the nucleic acid molecule of claim 1, and
   (c) an expression vector comprising the polynucleotide of (b).

4. The pharmaceutical composition of claim 3, wherein each B is the same or different.

5. The pharmaceutical composition of claim 3, wherein B is selected from the group consisting of SEQ ID NOs:4-7.

6. A recombinant DNA molecule that encodes the recombinant nucleic acid molecule of claim 1.

7. The recombinant DNA molecule of claim 6 that comprises one or more of SEQ ID NOs:4-7.

8. The recombinant nucleic acid molecule of claim 1, wherein the length of A is 0-20 nts.

9. The recombinant nucleic acid molecule of claim 1, wherein the length of A is 0-10 nts.

10. The recombinant nucleic acid molecule of claim 1, wherein the length of L is 0-20 nts.

11. The recombinant nucleic acid molecule of claim 1, wherein the length of L is 0-10 nts.

12. The recombinant nucleic acid molecule of claim 1, wherein the length of Z is 0-20 nts.

13. The recombinant nucleic acid molecule of claim 1, wherein the length of Z is 0-10 nts.

* * * * *

SEQUENCE LISTING

<160> NUMBER OF SEQ ID NOS: 13

<210> SEQ ID NO 1
<211> LENGTH: 21
<212> TYPE: RNA
<213> ORGANISM: Artificial sequence
<220> FEATURE:
<223> OTHER INFORMATION: siRNA

<400> SEQUENCE: 1
uucacuggac ucuucaccuc u                                             21

<210> SEQ ID NO 2
<211> LENGTH: 21
<212> TYPE: RNA
<213> ORGANISM: Artificial sequence
<220> FEATURE:
<223> OTHER INFORMATION: siRNA

<400> SEQUENCE: 2
uuagcaguug cucagccuga c                                             21

<210> SEQ ID NO 3
<211> LENGTH: 21
<212> TYPE: RNA
<213> ORGANISM: Artificial sequence
<220> FEATURE:
<223> OTHER INFORMATION: siRNA

<400> SEQUENCE: 3
aacaguuucg agcugccagg u                                             21

<210> SEQ ID NO 4
<211> LENGTH: 59
<212> TYPE: DNA
<213> ORGANISM: Artificial sequence
<220> FEATURE:
<223> OTHER INFORMATION: the DNA sequence for encoding precursor RNA

<400> SEQUENCE: 4
ttcactggac tcttcacctc tgttttggcc actgactgac agaggtgaag tccagtgaa    59

<210> SEQ ID NO 5
<211> LENGTH: 59
<212> TYPE: DNA
<213> ORGANISM: Artificial sequence
<220> FEATURE:
<223> OTHER INFORMATION: the DNA sequence for encoding precursor RNA

<400> SEQUENCE: 5
ttagcagttg ctcagcctga cgttttggcc actgactgac gtcaggctgc aactgctaa    59

<210> SEQ ID NO 6
<211> LENGTH: 59
<212> TYPE: DNA
<213> ORGANISM: Artificial sequence
<220> FEATURE:
<223> OTHER INFORMATION: the DNA sequence for encoding precursor RNA

<400> SEQUENCE: 6
aacagtttcg agctgccagg tgttttggcc actgactgac acctggcatc gaaactgtt    59

<210> SEQ ID NO 7
<211> LENGTH: 334
<212> TYPE: DNA
<213> ORGANISM: Artificial sequence

```
<220> FEATURE:
<223> OTHER INFORMATION: polynucleotide sequence formed by BTK-1-2-3 in
      tandem

<400> SEQUENCE: 7
tcactggact cttcacctct gttttggcca ctgactgaca gaggtgaagt ccagtgaaca      60
ggacacaagg cctgttacta gcactcacat ggaacaaatg gcccagatcc tggaggcttg    120
ctgaaggctg tatgctgtta gcagttgctc agcctgacgt tttggccact gactgacgtc    180
aggctgcaac tgctaacagg acacaaggcc tgttactagc actcacatgg aacaaatggc    240
ccagatcctg gaggcttgct gaaggctgta tgctgaacag tttcgagctg ccaggtgttt    300
tggccactga ctgacacctg gcatcgaaac tgtt                                334

<210> SEQ ID NO 8
<211> LENGTH: 19
<212> TYPE: DNA
<213> ORGANISM: Artificial sequence
<220> FEATURE:
<223> OTHER INFORMATION: primer

<400> SEQUENCE: 8
gaaggaggtt tcattgtca                                                  19

<210> SEQ ID NO 9
<211> LENGTH: 20
<212> TYPE: DNA
<213> ORGANISM: Artificial sequence
<220> FEATURE:
<223> OTHER INFORMATION: primer

<400> SEQUENCE: 9
taatactggc tctgaggtgt                                                 20

<210> SEQ ID NO 10
<211> LENGTH: 20
<212> TYPE: DNA
<213> ORGANISM: Artificial sequence
<220> FEATURE:
<223> OTHER INFORMATION: primer

<400> SEQUENCE: 10
ctccatcctg gcctcgctgt                                                 20

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
gctgtcacct tcaccgttcc                                                 20

<210> SEQ ID NO 12
<211> LENGTH: 19
<212> TYPE: DNA
<213> ORGANISM: Artificial sequence
<220> FEATURE:
<223> OTHER INFORMATION: primer

<400> SEQUENCE: 12
tgctcccact caatacaaa                                                  19
```

```
<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
gctctaccaa atgcctactc                                              20
```